United States Patent
Schulte

(10) Patent No.: US 8,579,808 B2
(45) Date of Patent: Nov. 12, 2013

(54) TENSIONING DEVICE OF A SURGICAL RETRACTOR

(75) Inventor: Hermann-Josef Schulte, Salzkotten (DE)

(73) Assignee: Condor GmbH Medicaltechnik, Salzkotten (DE)

( * ) Notice: Subject to any disclaimer, the term of this patent is extended or adjusted under 35 U.S.C. 154(b) by 0 days.

(21) Appl. No.: 13/127,273

(22) PCT Filed: Mar. 18, 2011

(86) PCT No.: PCT/DE2011/000283
§ 371 (c)(1),
(2), (4) Date: May 27, 2011

(87) PCT Pub. No.: WO2011/131162
PCT Pub. Date: Oct. 27, 2011

(65) Prior Publication Data
US 2013/0066162 A1    Mar. 14, 2013

(30) Foreign Application Priority Data

Apr. 19, 2010 (DE) .................. 20 2010 005 854 U

(51) Int. Cl.
*A61B 1/32* (2006.01)
(52) U.S. Cl.
USPC ........................................ 600/210

(58) Field of Classification Search
USPC ......... 600/210–215, 231–233, 219, 220, 224, 600/228, 229
See application file for complete search history.

(56) References Cited

U.S. PATENT DOCUMENTS

| 3,965,890 | A  | * | 6/1976 | Gauthier ................ 600/215 |
| 4,116,232 | A  | * | 9/1978 | Rabban ................ 600/215 |
| 6,416,470 | B2 | * | 7/2002 | Paolitto et al. ........ 600/232 |
| 8,357,184 | B2 | * | 1/2013 | Woolley et al. ........ 606/279 |
| 2008/0009884 | A1 | * | 1/2008 | Kennedy ................ 606/127 |

* cited by examiner

*Primary Examiner* — Pedro Philogene
(74) *Attorney, Agent, or Firm* — Laurence A. Greenberg; Werner H. Stemer; Ralph E. Locher

(57) ABSTRACT

A tensioning device of a surgical retractor has a tensioning section for applying a tensile force to a tool that is to be arranged thereon, and a holding bar fixed in position relative to the tensioning section, and also a locking device. The locking device is provided between the holding bar and the tensioning section and has a releasable locking function counter to the direction of the tensile force. The tensioning device can be operated comfortably, with minimal force being applied, is optimally accessible and takes up only a small overall volume. This is made possible by the fact that the locking device is configured as a linear ratchet or linear feed mechanism and that the feed mechanism has an actuating lever and an unlocking device.

6 Claims, 3 Drawing Sheets

TENSIONING DEVICE OF A SURGICAL RETRACTOR

BACKGROUND OF THE INVENTION

Field of the Invention

The invention relates to a tensioning device of a surgical retractor according to the preamble of the main claim.

Retractors of this kind are needed mainly in thoracic, pulmonary or cardiac surgery, in order to expose the operating site. A known tensioning device (U.S. Pat. No. 3,965,890) has a tensioning section, with a retractor hook arranged thereon, and a holding part fixed in position relative thereto, and, provided between these, a locking device with a releasable locking function counter to the direction of the tensile force. This tensile force is generated by a manual actuation, namely a pulling of the tensioning section by the locking device, which locks the tensioning section mechanically counter to an opposite movement.

A disadvantage of a known tensioning device of this kind is in particular that, in order to maneuver it when spreading-open the operating site, a considerable force has to be applied, since no force amplification is present, and the required force cannot be applied by every operator, especially also since the sometimes unfavorable spatial circumstances prevent optimal access to the tensioning device of the retractor.

BRIEF SUMMARY OF THE INVENTION

The object of the invention is to make available a tensioning device of a surgical retractor, which can be comfortably operated with minimal force being applied and which is optimally accessible and takes up only a small overall volume.

According to the invention, this object is achieved, in association with the features of the preamble, by the fact that the locking device is designed as a linear ratchet and/or linear feed mechanism, and the feed mechanism is provided with an actuating lever and an unlocking. It is thus possible, in a particularly simple manner using a mechanical actuating lever, to reduce the distance between a retractor hook and its positionally fixed arrangement on a retractor frame or on an operating table support, for which purpose different feed mechanisms can be used. The actuating lever reduces the force necessary for spreading-open the operating site and also shifts the point of application of force to an ergonomically advantageous area above the operating table.

Advantageous embodiments of the subject matter of the invention are set forth in combination in the dependent claims.

According to a particularly preferred embodiment of the invention, on the end of the tensioning section directed toward the holding bar, a receiver is provided for the holding bar, wherein the receiver is also designed at the same time as a housing for the feed mechanism, which feed mechanism has a pivot axis for the actuating lever and on which at least one first function part is arranged which generates a force-fit, form-fit and/or friction-fit connection, that can be canceled, to the tensioning section and with which the tensioning section can be moved a short distance in the direction of the holding bar. Moreover, in the actuating lever, a second function part is provided, which likewise has a force-fit, form-fit and/or friction-fit connection, that can be canceled, to the tensioning section and keeps the latter locked, when the actuating lever is pivoted back, counter to a restoring of the tensioning section.

By repeated actuation of the actuating lever, a retractor hook or other auxiliary means can accordingly be moved without application of any great force, particularly without this requiring an identically strong tensile force to be applied manually in the tensioning direction. By contrast, the overall volume additionally needed for the linear feed mechanism is more or less negligible.

According to a first advantageous embodiment of the subject matter of the invention, the first function part is composed of a locking lever, which has a locking lug and is pretensioned by a spring approximately parallel to the holding bar and is mounted pivotably in the actuating lever. The holding bar is provided along the length thereof with a latching track, and the locking lug of the locking lever engages in the latching track. The second function part likewise has a locking lug, wherein the first locking lug permits a movement of the tensioning section in the direction of the holding bar and the second locking lug locks a movement of the tensioning section counter to the tensile force.

In a second embodiment, a linear ratchet of this kind with single action is considerably improved by the fact that the holding bar is provided on both sides along its length with latching tracks arranged opposite each other, and the actuating lever engages around the holding bar, and the second function part is assigned to the opposite latching track, wherein the first and second function parts are both designed identically as locking levers with locking lugs, such that the locking levers can alternate in their function depending on the angle of pivoting of the actuating lever, as a result of which it is advantageously possible that, upon each stroke of the actuating lever, the tensioning section is moved by a small amount in the direction of the holding bar. This permits a more continuous and more uniform spreading-open of an operating site, and the force applied in both stroke movements of the actuating lever is identical, which improves the handling of the device.

The two locking levers, at their two ends opposite the locking lugs, are provided with lever ends via which the locking lugs, by a simultaneous pivoting movement about their pivot axes in the actuating lever, are movable from their locking engagement counter to an elastic restoring force, such that it is possible to quickly and easily unlock the tensioning section and, as a result, release the load on the retractor hook.

The pivot axis of the actuating lever is preferably formed by two guide pins extending from both sides of the holding bar through the head of the actuating lever and into the holding bar, wherein the holding bar is provided on both sides along its length with guide grooves into which these guide pins engage. This permits simple securing of the holding bar against rotation in the receiver of the tensioning section and also limits the movement of the tensioning section, wherein a further advantage of the tensioning device according to the invention is afforded by the fact that the guide pins are locked in the receiver and are designed to be removable therefrom, such that the entire tensioning device can be very easily dismantled for cleaning purposes.

The retractor hook can advantageously be locked with its cylindrical holding arm in another receiver of the tensioning section, by means of a spring-mounted unlocking pin being pressed for insertion of the holding arm and being let go to lock the latter, wherein the locking pin engages with its outer contour in a radial recess in the holding arm and locks the latter.

BRIEF DESCRIPTION OF THE SEVERAL VIEWS OF THE DRAWING

An illustrative embodiment of the invention is described in detail below with reference to drawings, in which.

DESCRIPTION OF THE INVENTION

Figure 1:
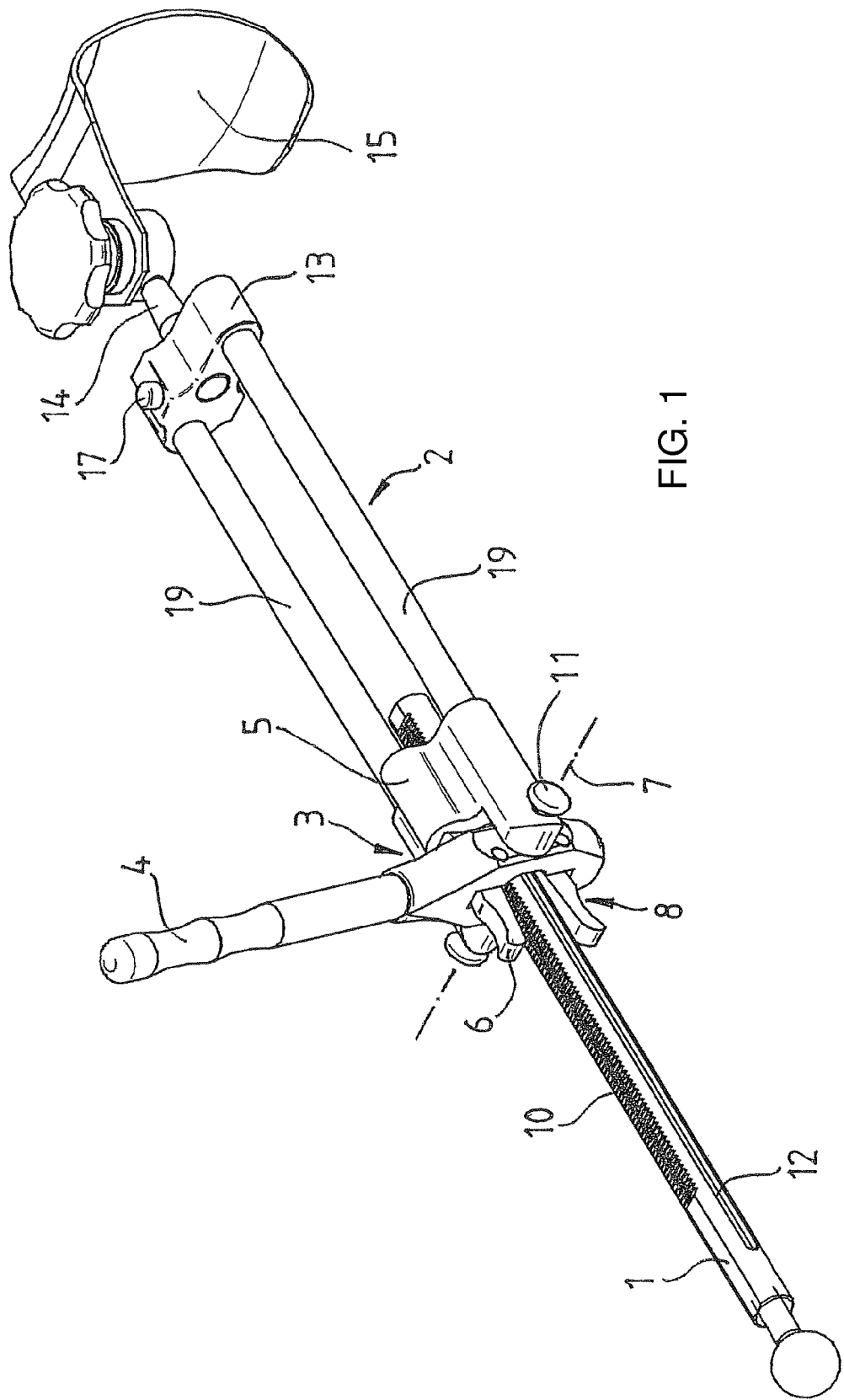
FIG. 1 shows a perspective view of the tensioning device with attached retractor hook.
Figure 2:
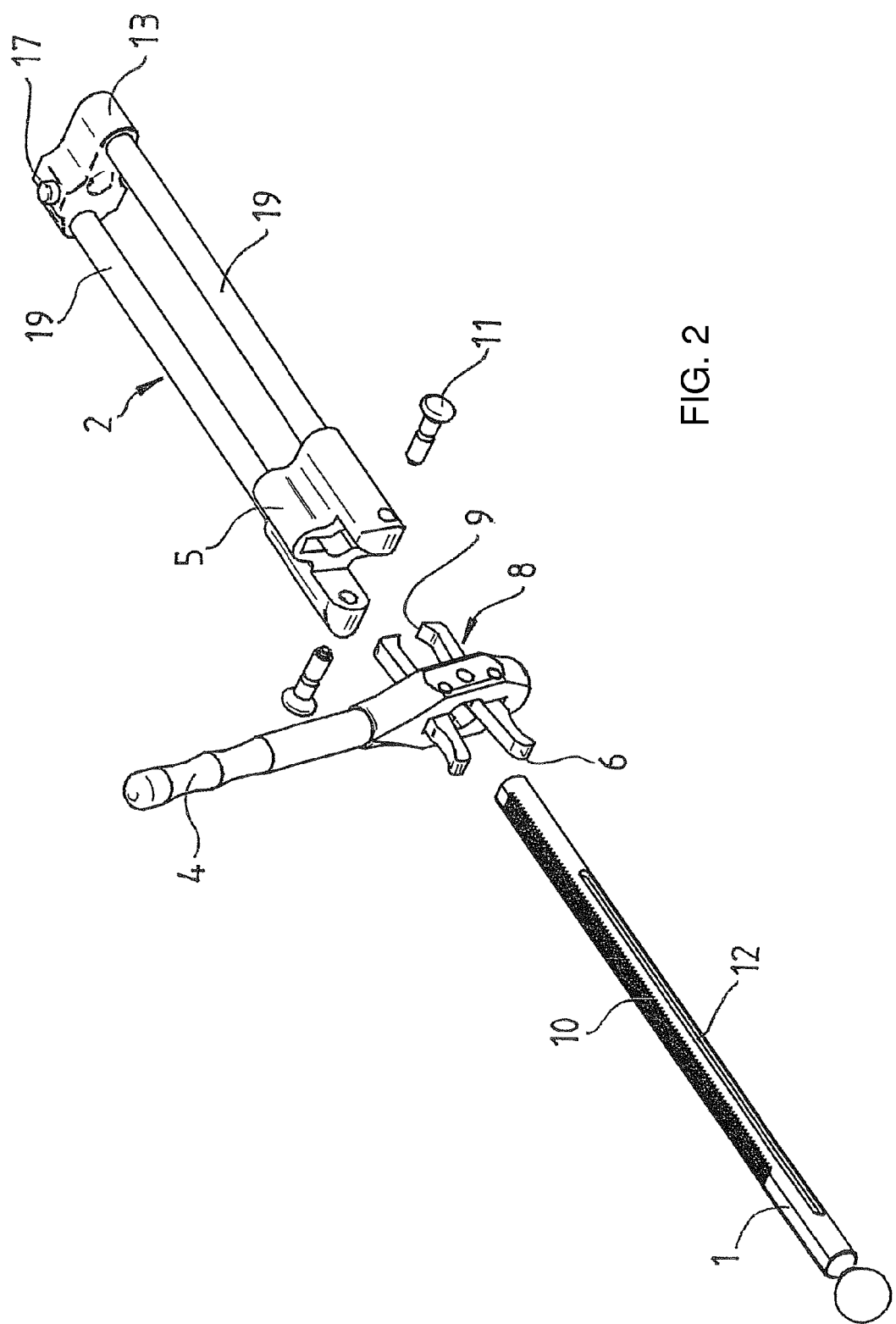
FIG. 2 shows an exploded view of the tensioning device according to FIG. 1.
Figure 3:
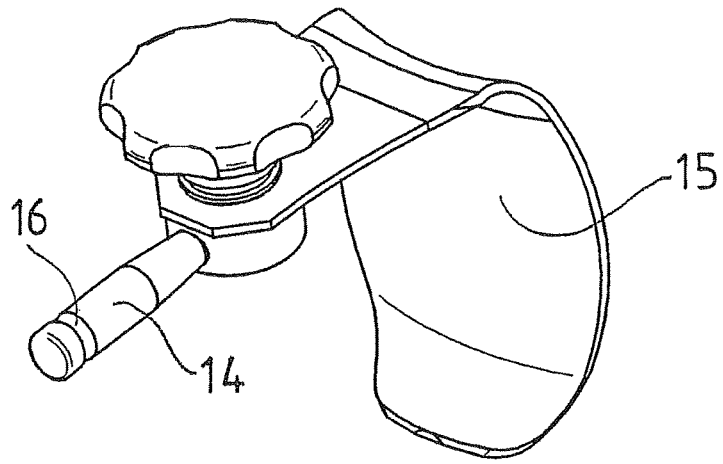
FIG. 3 shows a perspective view of a retractor hook.
Figure 4:
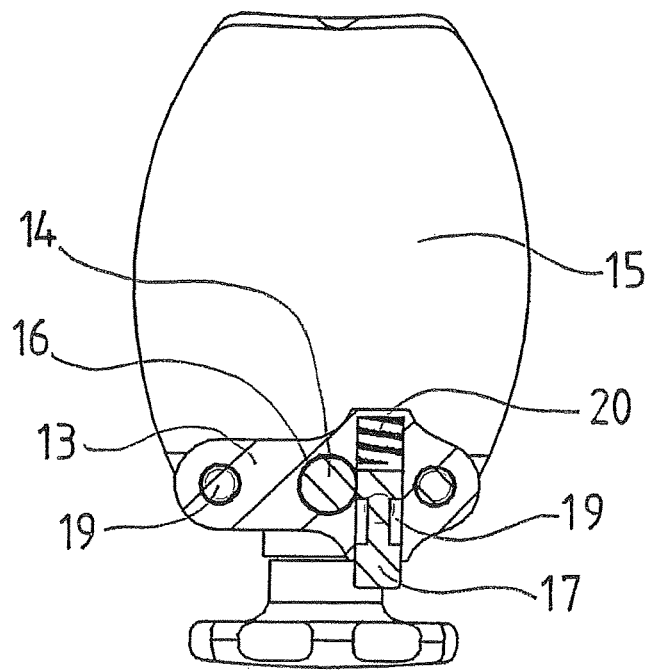
FIG. 4 shows a section through the receiver of the retractor hook according to FIG. 3.

The tensioning device of a surgical retractor is composed principally of a holding bar 1, which is fixed in position directly or indirectly on a retractor frame or on an operating table stand, and of a tensioning section 2, which is movable with respect to the holding bar 1 and which, at its end directed away from the holding bar 1, is provided with a receiver 13 for a retractor hook 15, which is arranged with a holding arm 14 in a corresponding bore of the receiver 13 and is held releasably there by a locking and unlocking pin 17, wherein the holding arm 14 of the retractor hook 15 has a radial recess 16 in which the body contour of the locking and unlocking pin 17 engages in a locking position and/or, when pressed counter to the spring force of a spring 20 in an unlocking position, frees the holding arm 14 for assembly or disassembly by way of radial recesses 18.

The holding bar 1 has two mutually opposite latching tracks 10 which extend along the greater part of the length thereof, and, at right angles thereto, two mutually opposite guide grooves 12 into which guide pins 11 project and thus, on the one hand, secure the holding bar 1 against rotation and, on the other hand, limit the movement of the holding bar 1. The guide pins 11 themselves have radial recesses, by means of which they are mounted releasably in the receiver 3 of the tensioning device via spring balls acting radially on the guide pins 11.

The guide pins 11 engage through the head part of the actuating lever 4 and thus form the pivot axis 7 of the latter. Approximately parallel to the latching tracks 10, locking levers 8 are mounted pivotably in the tension lever 4 where, with spring support, they are held with their locking lugs 9 pressed into notches of the latching track 10. At their ends opposite the locking lugs 9, the locking levers 8 are designed as lever ends 6 which, by a pivoting movement in the direction of the latching tracks, lift the locking lugs 9 from their locked state and thus permit a return of the tensioning section 2 to a starting position of the latter.

This feed mechanism functions as a linear ratchet which is active on both sides and which, upon a pivoting movement of the actuating lever 4 in the direction of the retractor hook, uses its locking lever 8 directed toward the actuating lever 4 to move the tensioning section 2 a few notches farther in the direction of the holding bar 1, wherein the opposite locking lever 8 jumps this number of notches of its latching track 10 and, upon a counter movement of the actuating lever 4, engages in notches of the latching track 10 and in turn moves the tensioning section 2 a few notches nearer to the holding bar 1, wherein the locking lever 8 arranged on the opposite side now in turn jumps a few notches of its latching track 10.

To unlock the mechanism, the two lever ends 6 of the locking levers 8 are pressed together in the direction of the latching tracks 10, wherein both locking lugs 9 of the locking levers 8 disengage, such that the tensioning section 2 can be pulled out without resistance. In addition to the receiver 13 for the retractor hook 15 and the receiver 3 for the ratchet mechanism, the tensioning section 2 itself has two rods 19, which are spaced apart and parallel and between which the holding bar 1 is movable, such that its symmetrical force distribution is maintained in the entire tensioning device. For pre-adjustment of the tensioning device, the tensioning section 2 and retractor hook 15 can be moved counter to the deflecting locking lugs 9 of the locking levers 8, and the retractor can be finely adjusted by the actuating lever 4.

The invention claimed is:

1. A tensioning device for a surgical retractor, the tensioning device comprising:
   a tensioning section for applying a tensile force to a tool that is to be disposed thereon;
   a holding bar fixed in position relative to said tensioning section, said tensioning section has an end directed toward said holding bar;
   a locking device disposed between said holding bar and said tensioning section and having a releasable locking function counter to a direction of the tensile force, said locking device selected from the group consisting of a linear ratchet and a linear feed mechanism, said linear feed mechanism having an actuating lever and an unlocking device;
   a receiver being disposed at said end of said tensioning section directed toward said holding bar, said receiver provided for said holding bar and is a housing for said linear feed mechanism, said housing having a pivot axis for said actuating lever;
   at least one first function part disposed on said actuating lever and generating a force-fit, a form-fit and/or a friction-fit connection, that can be canceled, to said tensioning section and with which said tensioning section can be moved in a direction of said holding bar;
   a second function part having a force-fit, a form-fit and/or a friction-fit connection, that can be canceled, to said tensioning section and keeps said tensioning section locked, when said actuating lever is pivoted back, counter to a restoring of said tensioning section;
   said first function part includes a spring and a locking lever with a locking lug and is pretensioned by said spring disposed approximately parallel to said holding bar and is mounted pivotably in said actuating lever;
   said holding bar has along a length of said holding bar a latching track, and said locking lug of said locking lever engages in said latching track;
   said second function part has a locking lug;
   said latching track is one of two latching tracks; and
   said holding bar has on both sides along said length said latching tracks disposed opposite each other, said actuating lever engages around said holding bar, said second function part engages on said opposite latching track, and in that both said first and second function parts are configured identically as said locking levers with said locking lugs, and in that said locking levers alternate in their function depending on the direction of pivoting of said actuating lever.

2. The tensioning device according to claim 1, wherein said locking lever, at its end opposite said locking lug, has a lever end via which said locking lug, by a pivoting movement about a pivot axis of said locking lever in said actuating lever, is movable from its locking engagement counter to an elastic restoring force.

3. The tensioning device according to claim 1, wherein said tensioning section applies the tensile force to a retractor hook.

4. A tensioning device for a surgical retractor, the tensioning device comprising:
- a tensioning section for applying a tensile force to a tool that is to be disposed thereon;
- a holding bar fixed in position relative to said tensioning section, said tensioning section has an end directed toward said holding bar;
- a locking device disposed between said holding bar and said tensioning section and having a releasable locking function counter to a direction of the tensile force, said locking device selected from the group consisting of a linear ratchet and a linear feed mechanism, said linear feed mechanism having an actuating lever and an unlocking device;
- a receiver being disposed at said end of said tensioning section directed toward said holding bar, said receiver provided for said holding bar and is a housing for said linear feed mechanism, said housing having a pivot axis for said actuating lever;
- at least one first function part disposed on said actuating lever and generating a force-fit, a form-fit and/or a friction-fit connection, that can be canceled, to said tensioning section and with which said tensioning section can be moved in a direction of said holding bar;
- a second function part having a force-fit, a form-fit and/or a friction-fit connection, that can be canceled, to said tensioning section and keeps said tensioning section locked, when said actuating lever is pivoted back, counter to a restoring of said tensioning section;
- two guide pins extending from both sides of said holding bar through said actuating lever and into said holding bar, said two guide pins defining said pivot axis; and
- wherein said holding bar has on both sides along its length guide grooves formed therein, into which said guide pins engage.

5. The tensioning device according to claim 4, wherein said guide pins are locked in said receiver and are configured to be removable therefrom, and in that said tensioning device can be dismantled for cleaning purposes.

6. The tensioning device according to claim 4, wherein:
- said tensioning section, at an end thereof directed away from said holding bar, has a receiver for a cylindrical holding arm of the tool being a retractor hook, and the holding arm has a radial recess formed therein; and
- said tensioning section further having an end pin/locking pin mounted resiliently in said receiver, extending orthogonally with respect to said receiver, and, in a locked state, engages with its outer contour in the radial recess of the holding arm.

* * * * *